United States Patent [19]

Paal et al.

[11] Patent Number: 5,212,186
[45] Date of Patent: May 18, 1993

[54] CARDIOACTIVE PYRROLOBENZIMIDAZOLES

[75] Inventors: Michael Paal, Hamburg; Wolfgang Stenzel, Reinbek; Reinhard Brückner, Hanover; Ben Armah, Hamburg, all of Fed. Rep. of Germany

[73] Assignee: Beiersdorf Aktiengesellschaft, Hamburg, Fed. Rep. of Germany

[21] Appl. No.: 750,372

[22] Filed: Aug. 27, 1991

[30] Foreign Application Priority Data

Aug. 31, 1990 [DE] Fed. Rep. of Germany ....... 4027592

[51] Int. Cl.$^5$ .................. A61K 31/44; A61K 31/415; C07D 487/04
[52] U.S. Cl. .................... 514/338; 514/394; 514/395; 514/278; 548/301.1; 548/302.1; 546/15; 546/271; 546/18; 546/82; 544/95
[58] Field of Search ........... 546/271; 548/326; 514/338, 394, 395, 278

[56] References Cited

U.S. PATENT DOCUMENTS 3,404,157 10/1968 McEvoy et al. ............. 548/371
4,207,318 6/1980 Rowlands ................. 544/101

FOREIGN PATENT DOCUMENTS

| 0098448 | 1/1984 | European Pat. Off. |
| 0161632 | 11/1985 | European Pat. Off. |
| 0173520 | 3/1986 | European Pat. Off. |
| 0186010 | 7/1986 | European Pat. Off. |
| 0214592 | 3/1987 | European Pat. Off. |
| 0318902 | 6/1989 | European Pat. Off. |
| 0322746 | 7/1989 | European Pat. Off. |
| 3417643 | 11/1985 | Fed. Rep. of Germany |
| 3445669 | 6/1986 | Fed. Rep. of Germany |
| 3446417 | 6/1986 | Fed. Rep. of Germany |
| 3501497 | 7/1986 | Fed. Rep. of Germany |
| 3524067 | 1/1987 | Fed. Rep. of Germany |
| 3531678 | 3/1987 | Fed. Rep. of Germany |
| 3626664 | 2/1988 | Fed. Rep. of Germany |
| 3633861 | 4/1988 | Fed. Rep. of Germany |
| 3639466 | 5/1988 | Fed. Rep. of Germany |
| 3642315 | 6/1988 | Fed. Rep. of Germany |
| 3701277 | 7/1988 | Fed. Rep. of Germany |
| 3840011 | 5/1990 | Fed. Rep. of Germany |
| 3911603 | 10/1990 | Fed. Rep. of Germany |
| 57-212188 | 12/1982 | Japan |
| 2002751 | 2/1979 | United Kingdom |
| 2082580 | 3/1982 | United Kingdom |

OTHER PUBLICATIONS

Chemical Abstracts, vol. 108, entries 87791d and 87792e, 1988, pp. 38–39.
Chemical Abstracts, vol. 111, entry 133f, 1989, pp. 9–10.
Chemical Abstracts, vol. 109, entry 122195g, 1988.
von der Saal et al., J. Med. Chem., 1989, 32, 1481–1491.
Mertens et al., J. Med. Chem. 1987, 30, 1279–1287.
Dorszewski et al., British Journal of Pharmacology, vol. 101(3), pp. 686–690, (1990).

Primary Examiner—Mary C. Lee
Assistant Examiner—Lenora Ava Miltenberger
Attorney, Agent, or Firm—Sprung Horn Kramer & Woods

[57] ABSTRACT

Compounds for the treatment of cardiac insufficiency, an arterial thrombo embolism, an arterial occlusive disease, psoriasis, neurodermatitis, asthma, platelet aggregation and hypertension, of the formula

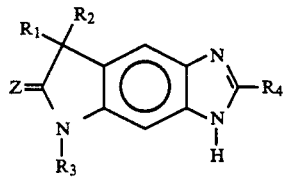

in which
$R_1$ is hydrogen, $C_{1-6}$-alkyl, $C_{2-6}$-alkenyl or $C_{3-7}$-cycloalkyl,
$R_2$ is hydrogen, $C_{1-6}$-alkyl, $C_{2-6}$-alkenyl or $C_{1-6}$-hydroxyalkyl,
$R_1$ and $R_2$ together with the carbon atom which carries them can be $C_{3-7}$-spiroalkyl,
$R_3$ is hydrogen or $C_{1-6}$-alkyl, and
$R_4$ is a cyanamido group, a 4-difluoromethoxy-3-pyridyl group or a $C_{1-2}$-nitroalkyl group, and
Z is oxygen or sulphur,
or a salt, acid addition salt, tautomer or optical isomer thereof.

6 Claims, No Drawings

CARDIOACTIVE PYRROLOBENZIMIDAZOLES

The invention relates to novel compounds of the formula I

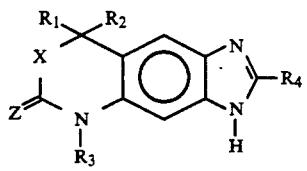

in which

X can have the meaning $X_a$, $X_a1$, $X_b$ or $X_c$, and in which in the case
a), in which X has the means $X_a$,
$X_a$ denotes the methylene group —CH$_2$—, and
$R_1$ has the meaning $R_{1a}$ and
$R_{1a}$ is hydrogen, $C_{1-6}$-alkyl, $C_{2-6}$-alkenyl or $C_{3-7}$-cycloalkyl and
$R_2$ has the meaning $R_{2a}$ and
$R_{2a}$ denotes hydrogen, $C_{1-6}$-alkyl, $C_{2-6}$-alkenyl or $C_{1-6}$-hydroxyalkyl, where $R_{1a}$ and $R_{2a}$ can be identical or different, or
$R_{1a}$ and $R_{2a}$, together with the carbon atom included by them, denote $C_{3-7}$-spiroalkyl,
$R^3$ denotes hydrogen or $C_{1-6}$-alkyl,
$R_4$ has the meaning $R_{4a}$ and
$R_{4a}$ denotes the cyanamido group, the 4-difluoromethoxy-3-pyridyl group or a $C_{1-2}$-nitroalkyl group and
Z denotes oxygen or sulphur, and in which in the case a$^1$), in which X has the meaning $X_a1$,
$X_a1$ together with $R_1$, which in this case has the meaning
$R_{1a}1$, denotes the group —CH= and
$R_2$ has the meaning $R_{2a}1$ and
$R_{2a}1$ is hydrogen or $C_{1-6}$-alkyl,
$R_3$ is hydrogen or $C_{1-6}$-alkyl,
$R_4$ has the meaning $R_{4a}1$ and
$R_{4a}1$ denotes the cyanamido group, the 4-difluoromethoxy-3-pyridyl group, a $C_{1-2}$-nitroalkyl group, hydrogen, the hydroxyl group, a mercapto, $C_{1-6}$-alkylsmercapto, an amino, pyridylcarbonylamino, $C_{1-6}$-alkylcarbonylamino, a $C_{1-6}$-alkyl, $C_{3-7}$-cycloalkyl, $C_{2-6}$-alkenyl, $C_{3-7}$-cycloalkenyl, $C_{2-6}$-alkynyl or $C_{1-6}$-haloalkyl group or a phenyl ring of the general formula II

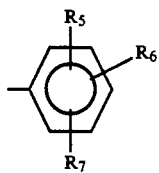

in which $R_5$, $R_6$ and $R_7$ can be identical or different and in each case can be hydrogen, a $C_{1-8}$-alkanesulphonyloxy, trifluoromethanesulphonyloxy, $C_{1-6}$-alkanesulphonylamino, trifluoromethanesulphonylamino, N-$C_{1-6}$-alkyl-$C_{1-6}$-alkylsulphonylamino, N-$C_{1-6}$-alkyltrifluoromethanesulphonylamino, $C_{1-6}$-alkylsulphenylmethyl, $C_{1-6}$-alkylsulphinylmethyl or $C_{1-6}$-alkylsulphonylmethyl group, a carbonyl group substituted by a hydroxyl, $C_{1-6}$-alkoxy, amino, $C_{1-6}$-alkylamino or $C_{2-12}$-dialkylamino group, a sulphonyl group substituted by an amino, $C_{1-6}$-alkylamino, $C_{2-12}$-dialkylamino or cyclic imino group, in which a methylene group in the 4-position can be replaced by a sulphur or oxygen atom, a $C_{1-6}$-alkylcarbonylamino, aminocarbonylamino or $C_{1-6}$-alkylaminocarbonylamino group, a $C_{1-6}$-alkylmercapto, $C_{1-6}$-alkylsulphinyl or $C_{1-6}$-alkylsulphonyl group, a nitro, halogen, amino, hydroxyl, $C_{1-6}$-alkyl, $C_{1-6}$-alkoxy, $C_{1-6}$-alkenyloxy, $C_{1-6}$-alkynyloxy, cyano-$C_{1-6}$-alkoxy, carboxy-$C_{1-6}$-alkoxy, $C_{1-6}$-alkoxycarbonyl-$C_{1-6}$-alkoxy, $C_{2-12}$-dialkylamino, 1-imidazolyl, trifluoromethyl or cyano group, or $R_{4a}1$ denotes a naphthyl radical or $R_{4a}1$ represents a saturated or unsaturated heterocyclic five-membered ring having 1-4 heteroatoms or a saturated or unsaturated heterocyclic six-membered ring having 1-5 heteroatoms, in which the heteroatoms can be identical or different and denote oxygen, sulphur or nitrogen and if desired can carry an oxygen atom on one or more nitrogen atoms, and the five-membered or six-membered rings can optionally be substituted by one or more $C_{1-6}$-alkyl, $C_{1-6}$-alkoxy, $C_{1-6}$-alkylmercapto, hydroxyl, nitro, amino, halogen or cyano groups or can be condensed with a phenyl ring to give a bicyclic compound and
Z denotes oxygen or sulphur, and in which in the case b), in which X has the meaning $X_b$,
$X_b$ denotes oxygen and
$R_1$ has the meaning $R_{1b}$ and $R_2$ the meaning $R_{2b}$ and $R_{1b}$ and $R_{2b}$, which can be identical or different, in each case stand for hydrogen or $C_{1-6}$-alkyl, $R_3$ denotes hydrogen or $C_{1-6}$-alkyl, $R_4$ has the meaning $R_{4b}$ and $R_{4b}$ is the cyanamido group, the 4-difluoromethoxy-3-pyridyl group or a $C_{1-2}$-nitroalkyl group and
Z denotes oxygen or sulphur, and in which in the case c), in which X has the meaning $X_c$, $X_o$ denotes a bond and
$R_1$ has the meaning $R_{1c}$ and
$R_{1c}$ is hydrogen, $C_{1-6}$-alkyl, $C_{1-6}$-alkenyl or $C_{1-6}$-cycloalkyl and
$R_2$ has the meaning $R_{2c}$ and
$R_{2c}$ denotes hydrogen, $C_{1-6}$-alkyl, $C_{2-6}$-alkenyl or $C_{1-6}$-hydroxyalkyl, in which $R_{1c}$ and $R_{2c}$ can be identical or different, or
$R_{1c}$ and $R_{2c}$, together with the carbon atom included by them, denote $C_{1-6}$-spiroalkyl,
$R_3$ denotes hydrogen or $C_{1-6}$-alkyl,
$R_4$ has the meaning $R_{4c}$ and
$R_{4c}$ is the cyanamido group, the 4-difluoromethoxy-3-pyridyl group or a $C_{1-2}$-nitroalkyl group and
Z denotes oxygen or sulphur, and their salts and acid addition salts, tautomers and optical isomers, process for their preparation, their use and preparations which contain these compounds.

For the sake of simplicity, the compounds according to the invention are defined in only one tautomeric form represented by formula I. However, the invention applies to all tautomeric forms of the compounds.

Although pharmaceutically tolerable salts and acid addition salts of the novel compounds of the formula I and their tautomeric forms are preferred, all salts are within the scope of the invention. All salts are useful for the preparation of the compounds, even if the specific salt is only desired as an intermediate, such as, for example, if the salt is only formed for the purposes of purification or identification, or if it is used as an intermediate in the preparation of a pharmaceutically tolerable salt, for example by means of an ion exchange procedure.

The compounds of the general formula I and their salts may contain asymmetric carbon atoms. The invention therefore also relates to the various optical isomers and the diastereoisomers as well as to the salts and addition salts of these compounds with acids. The racemates can be resolved into their optical antipodes by methods known per se.

Compounds of case a), where $X=X_a$ and the accompanying previously mentioned substituents are 7,8-dihydroimidazoquinolones, and correspondingly those of case $a^1$), where $X=X_a1$ are imidazoquinolones or, where $Z=S$, their thio analogues in each case.

The compounds of case b) where $X=X_b$ and the accompanying previously mentioned substituents form imidazobenzoxazinones or, where $Z=S$, their thio analogues in each case.

German Offenlegungsschriften 3,417,643, 3,501,497, 3,524,067, 3,532,678, 3,639,466 and 3,642,315 describe pyrrolobenzimidazoles variously substituted in the 2-position, DE-A-3,633,861 describes imidazobenzoxazinones and DE-A-3,701,277 describes imidazoquinolinones and medicaments containing these compounds for the treatment of cardiac and circulatory diseases.

The present invention relates on the other hand to pyrrolobenzimidazoles (X=valency), imidazobenzoxazinones (X=O) and imidazoquinolones (X=—CH$_2$—, —CH=) which are substituted in a novel manner in the 2-position. They have been neither specifically disclosed nor suggested.

By the following formulae Ia, Ia$^1$, Ib and Ic, the subformulae belonging to the abovementioned cases a), a$^1$), b) and c) are represented for the corresponding meanings of X mentioned in these formulae, where in this case therefore $X_a$ is CH$_2$, $X_a1$ is —CH, $X_b$ is O and $X_c$ is a bond:

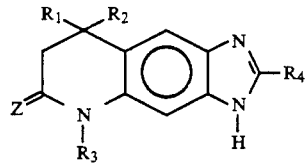
(Ia)

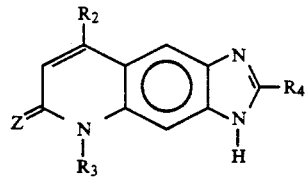
(Ia$^1$)

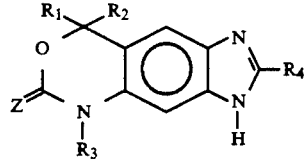
(Ib)

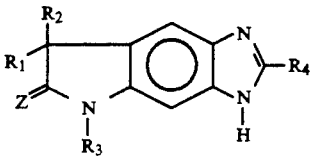
(Ic)

and the other substituents have the abovementioned meaning in each case.

The pyrrolobenzimidazoles of the formula I$_c$ corresponding to the case c) described above in which X or X$_c$ denotes a bond are particularly preferred

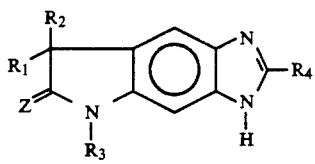
(Ic)

in which R$_{1c}$, R$_{2c}$, R$_3$, R$_{4c}$ and Z have the abovementioned meaning, and their salts and acid addition salts.

The alkyl groups and alkyl moieties according to the invention or alkylene moieties of groups can be straight-chain or branched and in each case, if not stated otherwise, preferentially have 1 to 6 carbon atoms, preferably 1 to 4 carbon atoms, in particular 1 or 2 carbon atoms. The branched alkyl groups have at least 3 carbon atoms. Preferred alkyl or alkylene moieties are methyl, ethyl, n-propyl, isopropyl, butyl or correspondingly methylene, ethylene, n- or isopropylene and butylene.

The alkene and alkyne groups according to the invention and alkene or alkyne moieties of groups can be straight-chain or branched and in each case, if not stated otherwise, preferentially have 2 to 6 carbon atoms, preferably 2 to 4 carbon atoms, in particular 2 or 3 carbon atoms.

Cycloalkyl groups and cycloalkyl moieties according to the invention such as cycloalkyl radicals of cycloalkylalkyl groups preferably have 3–7 carbon atoms, in particular 3 to 6 carbon atoms. Cyclopropyl and cyclohexyl are particularly preferred.

Cycloalkylene groups and cycloalkylene moieties of groups according to the invention preferably have 3 to 6 carbon atoms.

Halogen is fluorine, chlorine, bromine and iodine. Fluorine, chlorine or bromine is preferred.

Pyridylcarbonylamino is 2-, 3- or 4-pyridinyl-CO—NH—, C$_{1-6}$-alkylcarbonylamino is C$_{1-6}$-alkyl-CO—NH—, C$_{1-6}$-alkylaminocarbonylamino is C$_{1-6}$-alkyl-NH—CO—NH, and C$_{1-6}$-alkoxycarbonyl is C$_{1-6}$-alkoxy-CO—.

C$_{1-2}$-Nitroalkyl is preferably O$_2$N—CH$_2$—. Haloalkyl groups preferably have 1-3 halogen atoms, in particular one or two halogen atoms.

R$_4$ is preferably the cyanamido group —NH—CN.

If R$_{4a}1$ denotes a phenyl ring of the general formula II, the alkyl moiety of the substituents mentioned for R$_5$, R$_6$ and R$_7$ can also contain 1–5 carbon atoms, preferably 1–4 carbon atoms. In this sense, for example, the methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methylmethanesulphonylamino, N-ethylmethanesulphonylamino, N-methylethanesulphonylamino, N-ethylethanesulphonylamino, N-isopropylethanesulphonylamino, N-methyl-n-propanesulphonylamino, N-n-propyl-n-propanesulphonylamino, N-methyltrifluoromethanesulphonylamino, N-ethyltrifluoromethanesulphonylamino, N-isopropyltrifluoromethanesulphonylamino methoxycarbonyl, ethoxycarbonyl, propoxycarbonyl, isopropoxycarbonyl, methylaminocarbonyl, ethylaminocarbonyl, dimethylaminocarbonyl, Di-n-propylaminocarbonyl, N-methylethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, Di-n-propylaminosulphonyl, N-methylisopropylaminosulphonyl, acetylamino, propionylamino, methylcarbonylamino, ethylaminocarbonylamino or propylaminocarbonylamino group, or a methyl, ethyl, propyl, methoxy, ethoxy, propoxy, allyloxy, 2-butenyloxy, 3-butenyloxy, 2-pentenyloxy, propargyloxy, 2-butynyloxy, 3-butynyloxy, cyanomethyloxy, cyanoethyloxy, methoxycarbonylmethoxy, methoxycarbonylethoxy methylmercapto, ethylmercapto, methylsulphinyl, ethylsulphinyl, methylsulphonyl or ethylsulphonyl group are preferred.

In the case of sulphonyl groups which can be substituted by cyclic imino groups, the morpholino-, pyrrolidino-, piperidino- and hexamethyleneiminosulphonyl groups are preferred.

Particularly preferred for $R_5$ are hydrogen, an alkylsulphonyloxy, trifluoromethylsulphonyloxy, alkylsulphenylmethyl, alkylsulphinylmethyl, alkylsulphonylmethyl, alkylsulphonylamino, N-alkylalkylsulphonylamino, trifluoromethylsulphonylamino or N-alkyltrifluoromethylsulphonylamino group, a carbonyl group substituted by a hydroxyl, alkoxy, amino, alkylamino or dialkylamino group or a sulphonyl group substituted by an amino, dialkylamino or morpholino group in which each of the abovementioned alkyl moieties can contain 1 or 2 carbon atoms, a nitro, cyano or alkylaminosulphonyl group having 1–4 carbon atoms, an alkylcarbonylamino, aminocarbonylamino or N-alkylaminocarbonylamino group, an alkylmercapto, alkylsulphinyl or alkylsulphonyl group in which each of the abovementioned alkyl moieties can contain 1 or 2 carbon atoms, a halogen, amino, hydroxyl, dialkylamino, alkyl, alkoxy, alkenyloxy or alkynyloxy group preferably having 1–3 carbon atoms, a cyanomethoxy or methoxycarbonylmethoxy group, the trifluoromethyl group or the 1-imidazoyl group, for $R_6$ hydrogen, an alkyl group having 1–3 carbon atoms, an alkoxy or dialkylamino group having 1 to 2 carbon atoms on each alkyl moiety or a halogen atom, and for $R_7$ hydrogen or the methoxy group.

The phenyl moiety can carry 1 to 3 of the substituents mentioned.

Preferred monosubstituted phenyl compounds are the hydroxyl-, $C_1$-$C_3$alkyl-, $C_1$-$C_3$alkoxy-, allyloxy-, propargyloxy-, cyanomethoxy-, methoxycarbonylmethoxy-, halogeno-, nitro-, cyano-, aminocarbonyl-, methoxycarbonyl-, amino-,$C_1$-$C_3$dialkylamino-, $C_1$-$C_3$alkylmercapto-, $C_1$-$C_3$alkylsulphinyl-, $C_1$-$C_3$alkylsulphonyl-, $C_1$-$C_3$alkylsulphonyloxy- and the 1-imidazolylphenyls, in which the substituent can be in the 2-, 3- or 4-position.

Preferred disubstituted phenyls contain as substituents an alkanesulphonyloxy, trifluoromethylsulphonyloxy, alkylsulphenylmethyl,alkylsulphinylmethyl, alkylsulphonylmethyl, alkylsulphonylamino, N-alkylalkylsulphonylamino, trifluoromethylsulphonylamino or N-alkyltrifluoromethylsulphonylamino group, a carbonyl group substituted by a hydroxyl, alkoxy, amino, alkylamino or dialkylamino group or a sulphonyl group substituted by an amino, dialkylamino or morpholino group, an alkylaminosulphonyl, alkylcarbonylamino, aminocarbonylamino or N-alkylaminocarbonylamino group, a hydroxyl, alkyl, alkoxy, allyloxy, propargyloxy, cyanomethoxy, methoxycarbonylmethoxy, cyano, halogeno, nitro, amino, dialkylamino, alkylmercapto, alkylsulphinyl, alkylsulphonyl or a 1-imidazolyl group, in which the two substituents can be identical or different and can be in the 2,3-, 2,4-, 2,5-, 2,6-, 3,4- and 3,5-position, but preferably in the 2,4-, 2,5- and 3,4-position, and the abovementioned alkyl radicals, by themselves or in combination with other radicals, can have 1–3 C atoms.

A preferred trisubstituted phenyl radical is the 3,4,5-trimethyoxyphenyl radical.

If $R_{4a}1$ denotes a heterocyclic 5-membered ring having 1–4 heteroatoms or a heterocyclic 6-membered ring having 1–5 heteroatoms in which the heteroatoms of the abovementioned five-membered or six-membered rings can be identical or different and denote nitrogen, oxygen or sulphur and can optionally carry an oxygen on one or more nitrogen atoms, then in this sense the pyrrole, furan, thiophene, pyrazole, imidazole, thiazole, isothiazole, oxazole, isoxazole, triazole, tetrazole, thiadiazole, oxadiazole, pyrazine, pyrazine-N,N'-dioxide, pyrimidine, pyrimidine-N,N'-dioxide, pyridazine, oxazine, thiazine, triazine, tetrazine, pyridine, pyridine-N-oxide, piperidine, piperazine, morpholine and thiomorpholine radicals are preferred.

Alkyl, alkoxy and alkylmercapto substituents in the heterocyclic five-membered and six-membered rings can contain 1–6, preferably 1–4 carbon atoms. The methyl, ethyl, methoxy, ethoxy, methylmercapto and ethylmercapto radicals are preferred. Halogen is understood as meaning fluorine, chlorine and bromine, preferably chlorine.

If the heterocyclic five-membered and six-membered rings are fused to a phenyl ring, the indole, indazole, benzimidazole, quinoline, isoquinoline, cinnoline, phthalazine, quinazoline, quinoxaline, benzofuran, benzothiophene, benzoxazole, benzisoxazole, benzothiazole and benzisothiazole radical, in addition to the naphthyl radical are preferred If $R_{4a}1$ denotes an alkyl, alkenyl or alkynyl radical, then this is understood as meaning straight or branched chains having up to six C atoms. In this sense, the methyl, ethyl, propyl, butyl, pentyl, hexyl, vinyl, propenyl and propynyl radicals are preferred. If $R_{4a}1$ denotes a cycloalkyl or cycloalkenyl radical, then this is understood as meaning rings having three to seven members. In this sense, the cyclopropyl, cyclobutyl, cyclopentyl, cyclohexyl, cyclopentenyl and cyclohexenyl radicals are preferred. If $R_{4a}1$ denotes a haloalkyl, alkoxyalkyl, carboxyalkyl, alkoxycarbonylalkyl, hydroxyalkyl, aminoalkyl, alkoxycarbonylaminoalkyl, alkylsulphonylaminoalkyl, alkylmercapto or alkylcarbonylamino radical, then the alkyl or alkoxy groups can preferably contain 1 to 4 C atoms. Halogen is understood as meaning fluorine and chlorine, and preferably fluorine.

In this sense, the trifluoromethyl, ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylethyl, aminomethyl, aminoethyl, aminopropyl, aminobutyl, hydroxymethyl, hydroxyethyl, hydroxypropyl, hydroxybutyl, methylmercapto, ethylmercapto, propylmercapto, butylmercapto, acetylamino, propionylamino, butyloxycarbonylamino, methylsulphonylamino, formylaminopropyl, acetylaminopropyl, propionylaminopropyl and the methylsulphonylaminopropyl radical are preferred.

If in the general formula I $R_1$ and $R_2$ denote alkyl groups, then this is understood as meaning straight-chain or branched alkyl chains having 1-6 C atoms. In this sense, the methyl, ethyl, propyl and butyl group are preferred.

If $R_1$ and $R_2$, together with the C atom to which they are bonded, form a carbocyclic ring, then this is understood as meaning rings having three to seven members. The cyclopropane, cyclobutane, cyclopentane and cyclohexane ring are preferred.

Particularly preferred compounds are compounds of the general formula I in which $R_4$ denotes the cyanamido group or the phenyl radical of the general formula II in which $R_5$ denotes a hydrogen atom, the methanesulphonyloxy, trifluoromethanesulphonyloxy, methanesulphonylamino, trifluoromethanesulphonylamino, methylmercapto, methylsulphinyl, methylsulphonyl, hydroxyl, methyl, methoxy, propargyloxy, trifluoromethyl or the 1-imidazolyl group, $R_6$ denotes hydrogen, the methyl, methoxy, dimethylamino or chlorine group, $R_4$ denotes hydrogen or the methoxy group or R represents the pyrrole, furan, thiophene, pyrazole, imidazole, isothiazole, thiazole, oxazole, triazole, tetrazole, thiadiazole, isoxazole, oxadiazole, pyridine, pyridine-N-oxide, pyrazine, pyrazine-N,N'-dioxide, pyrimidine, pyrimidine-N,N'-dioxide, pyridazine, oxazine, thiazine, triazine, tetrazine, piperidine, piperazine, morpholine or thiomorpholine radical and their methyl-, ethyl-, methoxy-, ethoxy-, methylmercapto-, ethylmercapto- and chlorine-substituted derivatives or denotes the indole, indazole, quinoline or isoquinoline radical or represents a naphthyl radical, $R_1$ and $R_2$ are identical and denote methyl groups or $R_1$ and $R_2$, together with the carbon atoms to which they are bonded, form a cyclopentane ring or cyclohexane ring and $R_3$ denotes hydrogen, methyl, ethyl or propyl.

The following compounds according to the invention, their salts and acid addition salts, tautomers and optical isomers are preferred:

2-Cyanamido-6,7-dihydro-7,7-dimethyl-3H,5H-pyrrolo(2,3-f)benzimidazol-6-one

2-Cyanamido-5,7,7-trimethyl-6,7-dihydro-3H-pyrrolo(2,3-f)benzimidazol-6-one

2-Cyanamido-6,7-dihydro-7,7-cyclopropyl-3H,5H-pyrrolo (2,3-f)benzimidazol-6-one

2-Nitromethyl-6,7-dihydro-7,7-dimethyl-3H,5H-pyrrolo(2,3-f)benzimidazol-6-one 2-((4-Difluoromethoxy)-3-pyridyl)-6,7-dihydro-7,7-dimethyl-3H,5H-pyrrolo(2,3-f)benzimidazol-6-one 2-Cyanamido-8,8-dimethyl-8-hydro-5H-imidazo(4,5-g)(3,1)-benzoxazin-6-one 8,8-Dimethyl-2-nitromethyl-8-hydro-5H-imidazo(4,5-g)-(3,1)benzoxazin-6-one 8,8-Dimethyl-2-(4-difluoromethoxy-3-pyridyl)-8-hydro-5H-imidazo(4,5-g)(3,1)benzoxazin-6-one 2-Methyl-3H,5H-imidazo(4,5-g)quinolin-6-one 2-Trifluoromethyl-3H,5H-imidazo(4,5-g)quinolin-6-one 2-(4-Pyridyl)-3H,5H-imidazo(4,5-g)quinolin-6-one 2-(3-Pyridyl)-3H,5H-imidazo(4,5-g)quinolin-6-one 2-Cyanamido-7,8-dihydro-3H,5H-imidazo(4,5-g)quinolin-6-one 2-Cyanamido-3H,5H-imidazo(4,5-g)quinolin-6-one 2-(4-Methylthiophenyl)-3H,5H-imidazo(4,5-g)quinolin-6-one 2-(4-Methoxyphenyl)-3H,5H-imidazo(4,5-g)quinolin-6-one 2-(4-(1H-Imidazol-1-yl)-phenyl)-3H,5H-imidazo(4,5-g)-quinolin-6-one 2-(4-(Trimethylsulphinyl)-phenyl-3H,5H-imidazo-(4,5-g)quinolin-6-one The compounds of the formula I according to the invention, their physiologically tolerable salts and acid addition salts and their tautomeric and optical isomers are therapeutic active substances, have high pharmacological activity and are useful medicaments. For example, they are inhibitors of PDE-III and PDE-IV. They preferably have cardiovascular properties and effects. They are distinguished in particular by vasodilatory, hypotensive, positive inotropic and antithrombotic effects.

The compounds according to the invention are suitable for the treatment and prophylaxis of chronic and acute cardiac insufficiency of various origin and/or for the treatment and prophylaxis of arterial thromboembolisms and arterial occlusive diseases in warm-blooded animals, in particular humans.

The compounds according to the invention in particular have hypotensive activity and can thus be used as antihypertensive agents for the treatment and prophylaxis of hypertension.

In addition, they can be used for the treatment and prophylaxis of psoriasis, neurodermatitis and asthma, in particular bronchial asthma. The compounds inhibit platelet aggregation. They can be used for the treatment and prophylaxis of thromboembolic diseases The compounds of the present invention can be administered orally or parenterally.

For this purpose, the novel compounds, if appropriate in combination with other active substances, can be incorporated in particular into the customary pharmaceutical administration forms such as tablets, coated tablets, powders, suspensions, suppositories or ampoules. For example, the individual dose in this case in adults is in each case 1-50 mg, preferably 2 to 40 mg, once to four times daily on intravenous administration and 5-150 mg, preferably 5 to 100 mg, on oral administration.

The compounds according to the invention are customarily administered in amounts of 10-500 mg per day relative to a body weight of 75 kg. It is preferred to administer 1-2 tablets having an active substance content of 2-20 mg 2-3 times per day. The tablets can also be of the sustained-release type, as a result of which 1-2 tablets containing 10-500 mg of active substance have to be given only once per day. The active substance can also be given by injection 1-8 times per day or by continuous infusion, amounts of 5-200 mg/day normally being sufficient. These dosages are advantageous for the treatment of the diseases mentioned, in particular hypertension.

The substances according to the invention are distinguished by a considerable lowering of the arterial blood pressure. Doses of about 1 mg/kg p.o. lead to a lowering of the blood pressure of at least 20% in hypertensive rats.

In spite of this, it may be necessary to deviate from the amounts mentioned, in particular depending on the body weight or the type of administration route, but also as a result of the individual behaviour towards the medicament or the manner of its formulation and the time or interval at which administration takes place. Thus, in some cases it may be sufficient to manage with less than the abovementioned minimum amount, while in other cases the upper limit mentioned must be exceeded. In the case of administration of larger amounts, it may be advisable to divide these into several individual doses over the course of the day.

The treatment of skin diseases, neurodermatitis or psoriasis can also be carried out topically. For treatment, for example, creams, lotions, ointments, solutions or powders are suitable which contain the active substance preferably in an amount of 1-10 %. For prophylaxis or treatment, a topical preparation is applied in a thin layer to the skin or the diseased skin once or several times daily.

The invention also relates to the compounds according to the invention for the treatment of the abovementioned diseases and to methods for the treatment of these diseases in which these compounds are used and to their use in processes for the production of compositions which contain these compounds, for the treatment of these diseases and to processes for the preparation of the compounds.

According to the invention, pharmaceutical preparations or compositions are provided which contain a compound according to the invention or its pharmaceutically tolerable salt or acid addition salt, if appropriate together with a pharmaceutically tolerable diluent or excipient, and also topical preparations containing these compounds according to the invention.

The compounds according to the invention can be mixed with customary pharmaceutically tolerable diluents or excipients and optionally with other auxiliaries and, for example, administered orally or parenterally. They may preferably be administered orally in the form of granules, capsules, pills, tablets, film tablets, coated tablets, syrups, emulsions, suspensions, dispersions, aerosols and solutions as well as liquids, or parenterally in the form of solutions, emulsions or suspensions. Preparations to be administered orally may contain one or more additives such as sweeteners, flavourings, colourants and preservatives. Tablets may contain the active substance mixed with customary pharmaceutically tolerable auxiliaries, for example inert diluents such as calcium carbonate, sodium carbonate, lactose and talc, granulating agents and agents which promote the disintegration of the tablets on oral administration, such as starch or gelatin, and lubricants such as magnesium stearate, stearic acid and talc.

Suitable excipients are, for example, milk sugar (lactose), gelatin, maize starch, stearic acid, ethanol, propylene glycol, ethers of tetrahydrofurfuryl alcohol and water.

Examples of auxiliaries which may be mentioned are: water, non-toxic organic solvents, such as paraffins (for example mineral oil fractions), vegetable oils (for example groundnut/sesame oil), alcohols (for example ethyl alcohol, glycerol, glycols (for example propylene glycol, polyethylene glycol), solid excipients, such as, for example, ground natural minerals (for example kaolins, silicas, talc, chalk), ground synthethic minerals (for example highly disperse silicic acid, silicates), sugars (for example sucrose, lactose and dextrose), emulsifiers (for example polyoxyethylene fatty acid esters, polyoxyethylene fatty alcohol ethers, alkylsulphonates and arylsulphonates, dispersing agents (for example methylcellulose, starch and polyvinylpyrrolidone) and lubricants (for example magnesium stearate, talc, stearic acid and sodium lauryl sulphate).

The formulations are prepared, for example, by extending the active substances using solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular perlingually or intravenously. In the case of oral administration, in addition to the excipients mentioned, tablets can of course also contain additives, such as sodium citrate, calcium carbonate and dicalcium phosphate together with various additional substances, such as starch, preferably potato starch, gelatin and the like. In addition, lubricants such as magnesium stearate, sodium lauryl sulphate and talc can also be used for tableting. In the case of aqueous suspensions and/or elixirs which are intended for oral administration, various flavour enhancers or colourants can be added to the active substances in addition to the abovementioned auxiliaries.

In the case of parenteral administration, solutions of the active substances can be employed using suitable liquid excipient materials.

The tablets can be coated by known procedures in order to delay disintegration and absorption in the gastrointestinal tract, as a result of which the activity of the active substance can be extended over a relatively long period of time. In the suspensions, the active substance can also be mixed with auxiliaries which are customary for the preparation of such compositions, for example suspending agents such as methylcellulose, tragacanth or sodium alginate, wetting agents such as lecithin, polyoxyethylene stearate and polyoxyethylene sorbitan monooleate and preservatives such as ethyl parahydroxybenzoate. Capsules may contain the active substance as a single constituent or mixed with a solid diluent such as calcium carbonate, calcium phosphate or kaolin. The injectable preparations are also formulated in a manner known per se.

The pharmaceutical preparations can contain the active substance in an amount from 0.1 to 90 per cent by weight, in particular 1 to 90 per cent by weight, i.e. in amounts which are sufficient in order to achieve the dosage range indicated, the remainder being an excipient or additive. With respect to preparation and administration, solid preparations such as tablets and capsules are preferred. The preparations preferably contain the active substance in an amount of 2 to 80 mg.

The compounds according to the invention can be obtained by the following process: From compounds of the formula III

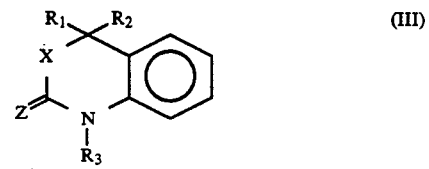

(III)

which are accessible by processes known from the literature and in which $R_1$, $R_2$, $R_3$, X and Z have the meaning indicated, compounds of the general formula IV

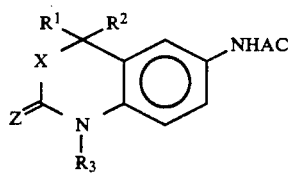
(IV)

in which $R_1$, $R_2$, $R_3$, X and Z are defined as at the start, are obtained by nitration with fuming nitric acid (d=1.52), subsequent hydrogenation in the presence of Raney nickel and introduction of an acetyl protective group AC.

By further treatment with fuming nitric acid (d=1.52), compounds of the general formula V

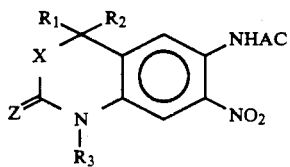
(V)

can be prepared, which by subsequent removal of the acetate protective group by known methods, give compounds of the general formula VI

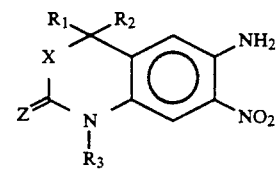
(VI)

in which $R_1$, $R_2$, $R_3$, X and Z have the meanings indicated. The compounds of the formula VI are a) either reacted with compounds of the formula VII

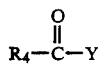
(VII)

in which $R_4$ has the meaning indicated and Y denotes a hydrogen atom, the hydroxyl group, halogen or an easily removable group, so that, for example, aldehydes, preferably carboxylic acids or carboxylic acid derivatives, are meant by formula VII, and the reaction products are then hydrogenated and cyclised under acidic conditions, as a result of which compounds of the formula I are obtained, or b) hydrogenated with Raney nickel to give compounds of the general formula VIII

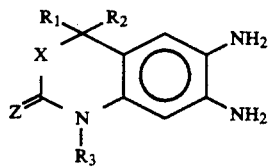
(VIII)

in which $R_1$, $R_2$, $R_3$, X and Z have the meanings indicated.

The compounds of the formula VIII can be converted by reaction with the compounds of the formula VII into compounds of the formula IX or its isomers

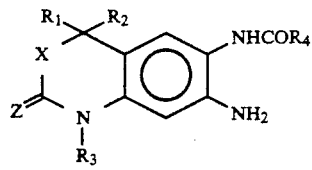
(IX)

in which $R_1$, $R_2$, $R_3$, $R_4$, X and Z have the meanings indicated, and can be converted into compounds of the general formula I by cyclisation.

If the compound VII mentioned in process a) is a carboxylic acid, the reaction with compounds of the general formulae VI and VIII is preferably carried out in aprotic solvents such as tetrahydrofuran or dioxane at temperatures between 0° C. and the boiling temperature of the solvent. If the compound VII in process a) is a carboxylic acid derivative, for example a carboxylic acid chloride, the reaction is carried out in an inert solvent such as methylene chloride or pyridine at temperatures between 0° C. and the boiling temperature of the solvent.

The reduction mentioned in process a) is preferably carried out in a solvent or solvent mixture such as water, methanol, ethanol, glacial acetic acid, ethyl acetate or dimethylformamide with hydrogen in the presence of a catalyst such as Raney nickel, platinum or palladium/carbon, with metals such as iron, tin or zinc in the presence of an acid, with salts such as iron(II) sulphate, tin(II) chloride, sodium sulphide, sodium hydrogen sulphite or sodium dithionite or with hydrazine in the presence of Raney nickel at temperatures between 0° and 100° C., but preferably at room temperature. The cyclised compounds of the general formula I are usually formed immediately in this way.

If desired, the cyclisation can be completed by heating to temperatures between 50° and 220° C., but preferably to the boiling temperature of the reaction mixture, if appropriate in the presence of a condensing agent such as phosphorus oxychloride, thionyl chloride, p-toluenesulphonic acid, hydrochloric acid, sulphuric acid, phosphoric acid, polyphosphoric acid or if appropriate also in the presence of a base such as sodium hydroxide, sodium ethoxide or potassium tert-butoxide after the reduction, preferably in a solvent or solvent mixture such as ethanol, isopropanol, glacial acetic acid, benzene, toluene, chlorobenzene, glycol, ethylene glycol dimethyl ether, sulpholane or dimethylformamide. However, the cyclisation can also be carried out without solvent and/or condensing agent.

If the compound of the general formula VII in process b) is a carboxylic acid, the reaction with compounds of the general formula V takes place in the presence of a dehydrating agent, preferably in polyphosphoric acid at temperatures between 50° and 250° C., preferably between 100° and 200° C.

If the compound of the general formula VII is a carboxylic acid derivative, the reaction with compounds of the general formula VIII takes place in an inert solvent, preferably in methylene chloride or pyridine. To complete the cyclisation, the mixture is then heated in a solvent or solvent mixture such as ethanol, isopropanol, glacial acetic acid, toluene or dimethyl-formamide to temperatures between 50° C. and the boiling temperature of the solvent.

The conversion of compounds of the general formula V in which X denotes a $CH_2$ group and $R_1$ and $R_2$ denote hydrogen or alkyl to other compounds of the formula V in which X denotes a CH group, $R_1$ denotes a valency and $R_2$ denotes hydrogen or alkyl can be effected by the use of suitable oxidising agents such as, for example, manganese dioxide or dichlorodicyanobenzoquinone in suitable solvents such as DMF, THF or dioxane, preferably at the boiling temperature of these solvents. Compounds of the formula X

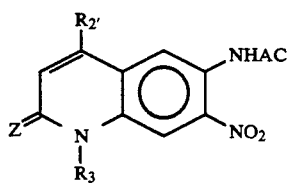

are obtained in which $R_3$, AC and Z have the meaning indicated and $R_2$ is hydrogen or alkyl, and can be converted into compounds of the general formula XI

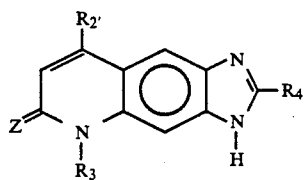

in which $R_2$, $R_3$, $R_4$ and Z have the meanings mentioned, in the manner described above The conversion of compounds of the general formula I to other compounds of the general formula I applies for example A. To the reaction of a compound in the cases a) and $a^1$) in which $R_4$ represents an amino, aminoalkyl or cyclic imino group, or a heterocyclic five-membered or six-membered ring substituted by an amino group, or a phenyl ring of the general formula II, in which one or more of the substituents $R_5$, $R_6$ and $R_7$ represent an amino group, and/or in which $R_3$ represents a hydrogen atom, with carboxylic acids or with activated carboxylic acid derivatives such as anhydrides or acid halides to give formylamino or alkylcarbonylamino derivatives. Reactions with carboxylic acids are preferably carried out in the presence of a dehydrating agent such as, for example, polyphosphoric acid or of a solvent forming an azeotropic mixture with water, such as benzene or toluene Reactions with activated carboxylic acid derivatives are preferably carried out in inert solvents such as methylene chloride or pyridine at temperatures between 0° C. and 250° C., but preferably at the boiling temperature of the solvent.

B. To the reaction of compounds of cases a) and $a^1$) in which $R_4$ represents an amino, aminoalkyl or cyclic imino group, or $R_4$ represents a heterocyclic five-membered or six-membered ring substituted by an amino group, as is defined at the start, or $R_4$ represents a phenyl ring of the general formula II in which one of the substituents $R_5$, $R_6$ or $R_7$ represents an amino, N-alkylamino or hydroxyl group, with a sulphonic acid of the general formula XII $$R_8-SO_2OH \qquad (XII)$$

in which $R_8$ represents an alkyl group having 1-3 carbon atoms or a trifluoromethyl group or with a reactive derivative thereof, to give compounds of a) and $a^1$) in which the said amino, aminoalkyl, cyclic imino, N-alkylamino or hydroxyl groups are sulphonated. The reaction is expediently carried out in a solvent or solvent mixture such as methylene chloride, ether, tetrahydrofuran, dioxane or benzene, if appropriate in the presence of an acid-binding agent such as sodium carbonate, triethylamine or pyridine, it also being possible to use the latter two at the same time as the solvent, in the presence of an acid-activating or dehydrating agent such as thionyl chloride or phosphorus pentachloride, but preferably with a reactive derivative of a compound of the general formula XII, for example with its anhydride or halide such as methanesulphonyl chloride or ethanesulphonyl chloride, preferably at temperatures between 0° and 100° C., for example at temperatures between room temperature and 50° C.

C. To the conversion of compounds of a) and a ) in which $R_4$ represents a phenyl group of the general formula II, in which one of the substituents $R_5$, $R_6$ or $R_7$ is an alkylmercapto or alkylsulphenylmethyl group having 1-3 carbon atoms in the alkyl moiety, to give compounds of a) and $a^1$) in which $R_1$ represents a phenyl group and one of the substituents $R_5$, $R_6$ and $R_7$ represents an alkylsulphinyl, alkylsulphonyl, alkylsulphinylmethyl or alkylsulphonylmethyl group.

This oxidation is preferably carried out in a solvent or solvent mixture, for example in water, water/pyridine, acetone, glacial acetic acid, dilute sulphuric between −80° and 100° C. depending on the oxidising agent used. To prepare an alkylsulphinyl or alkylsulphinylmethyl compound of the general formula I, the oxidation is expediently carried out with one equivalent of the oxidising agent used, for example with hydrogen peroxide in glacial acetic acid, trifluoroacetic acid or formic acid at 0° to 20° C. or in acetone at 0° to 60° C., with a peracid such as performic acid in glacial acetic acid or trifluoroacetic acid at 0° to 50° C. or with m-chloroperbenzoic acid in methylene chloride or chloroform at −20° C. to 60° C., with sodium metaperiodate in aqueous methanol or ethanol at −15° to 25° C., with bromine in glacial acetic acid or aqueous acetic acid, with N-bromosuccinimide in ethanol, with tert-butyl hypochlorite in methanol at −80° C. to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphuryl chloride in methylene chloride at −70° C.; the thioetherchlorine complex obtained in this case is expediently hydrolysed with aqueous ethanol.

To prepare an alkylsulphonyl compound of a) and $a^1$), the oxidation is expediently carried out with one or with two or more equivalents of the oxidising agent used, for example hydrogen peroxide in glacial acetic acid, trifluoroacetic acid or in formic acid at 20° to 100° C. or in acetone at 0° to 60° C., with a peracid such as performic acid, or m-chloroperbenzoic acid in glacial acetic acid, trifluoroacetic acid, methylene chloride or chloroform at temperatures between 0° and 60° C., with nitric acid in glacial acetic acid at 0° to 20° C., with chromic acid or potassium permanganate in glacial acetic acid, water/sulphuric acid or in acetone at 0° to 20° C.

D. To the conversion of compounds of a) and $a^1$) in which $R_4$ represents a phenyl group of the general formula II, in which one of the substituents $R_5$, $R_6$ and $R_7$ represents a carboxyl or hydroxysulphonyl group, to compounds of a) and a¹) in which one of the substituents $R_5$, $R_6$ and $R_7$ represents a carbonyl or sulphonyl group substituted by an amino, alkylamino or dialkylamino group. This is carried out by reaction with an amine $HNR_9R_{10}$ in which $R_9$ and $R_{10}$ can be identical or different and denote hydrogen or $C_1-C_5$ alkyl groups, or with a reactive derivative thereof. It is advantageous to convert the carboxyl group or hydroxysulphonyl group into a reactive derivative, for example into an ester or an acid chloride, and then to react with the amine $HNR_9R_{10}$.

The reaction is expediently carried out in a solvent or solvent mixture such as methylene chloride, ethanol, chloroform, carbon tetrachloride, ether, tetrahydrofuran, dioxane, benzene, toluene, acetonitrile or dimethylformamide, if appropriate in the presence of an acid-activating agent or a dehydrating agent, for example in the presence of ethyl chloroformate, thionyl chloride, phosphorus trichloride, phosphorus pentoxide, N,N'-dicyclohexylcarbodiimide/N-hydroxysuccinimide, N,N'-carbonyldiimidazole or N,N'-thionyldiimidazole or triphenylphosphine/carbon tetrachloride, or of an amino group-activating agent, for example phosphorus trichloride, and if appropriate in the presence of an inorganic base such as sodium carbonate or a tertiary organic base such as triethylamine or pyridine, which can be used at the same time as the solvent, at temperatures between −25° and 250° C., but preferably at temperatures between −10° C. and the boiling temperature of the solvent used; in addition, water formed during the reaction can be removed by azeotropic distillation, for example by heating with toluene in a water separator, or by addition of a drying agent such as magnesium sulphate or molecular sieve.

However, the reaction is particularly advantageously carried out in an appropriate halide, for example the carboxylic acid or sulphonic acid chloride, and an appropriate amine, it being possible for this to serve simultaneously as the solvent, and at temperatures between 0° and 50° C.

E. To the conversion of compounds of a) and a¹) in which $R_1$ represents a phenyl ring of the general formula II and one of the substituents $R_5$, $R_6$ or $R_7$ represents the cyano group and/or in which $R_3$ represents an alkanoyl radical, to compounds of the general formula I in which $R_1$ represents a phenyl ring of the general formula II and one of the substituents $R_5$, $R_6$ or $R_7$ denotes an alkoxycarbonyl group, an aminocarbonyl group or a carboxyl group, and/or in which $R_3$ represents a hydrogen atom.

This alcoholysis and/or hydrolysis is carried out either in the presence of an acid such as hydrochloric acid, sulphuric acid, phosphoric acid or trichloroacetic acid or in the presence of a base such as sodium hydroxide or potassium hydroxide in a suitable solvent such as water, water/methanol, ethanol, water/ethanol, water/isopropanol or water/dioxane at temperatures between −10° and 120° C., for example at temperatures between room temperature and the boiling temperature of the reaction mixture.

F. To the alkylation of compounds of a) and a¹) in which $R_4$ represents a phenyl ring of the general formula II, in which one of the substituents $R_5$, $R_6$ or $R_7$ denotes a hydroxyl or mercapto group, or in which $R_4$ represents a heterocyclic ring substituted by a hydroxyl or mercapto group. The corresponding alkylmercapto or alkoxy compounds are formed in this case.

The reactions are preferably carried out in a solvent such as acetone, ether, benzene, toluene or dimethylformamide at temperatures between −30° C. and +100° C., preferably at room temperature in the presence of a base such as potassium carbonate or sodium hydride and of an alkylating agent such as alkyl halides or alkyl sulphates.

G. To the reduction of compounds of a) and a¹) in which $R_4$ represents a pyridine ring, to compounds of a) and a¹) in which $R_4$ denotes the piperidine ring. These reductions are preferably carried out by means of hydrogen at normal pressure or slightly elevated pressure and of a temperature between room temperature and 60° C. in alcoholic medium in the presence of a catalyst such as platinum or palladium.

H. To the oxidation of a five-membered or six-membered ring having one or more nitrogen atoms to the corresponding N-oxides. The oxidation is expediently carried out with one or more equivalents of the oxidising agent used, for example with hydrogen peroxide in glacial acetic acid, trifluoroacetic acid or in formic acid at 20°–100° C. or in acetone at 0°–60° C., with a peracid such as performic acid or m-chloroperbenzoic acid in glacial acetic acid, trifluoroacetic acid, methylene chloride or chloroform at temperatures between 0° and 60° C.·

The starting compounds of the formulae III to XII are known or can be obtained by known processes.

The compounds of the general formula I can be either bases or acids or can be amphoteric and are therefore isolated from the reaction mixtures in the form of their salts or acid addition salts. As bases, they can be converted into salts by known processes using suitable inorganic or organic acids or, as acids, form salts with bases.

Physiologically tolerable salts or acid addition salts are preferred. For this purpose, hydrohalic acids, for example hydrochloric acid, or sulphuric acid are suitable as inorganic acids, and, for example, fumaric acid, maleic acid, citric acid and tartaric acid are suitable as organic acids. For preparation, the hot alcoholic solution of the base is treated with the alcoholic solution of a suitable acid, and the salt is obtained after addition of ether. Preferred salts are the alkali metal, alkaline earth metal and ammonium salts of the compounds of the formula I, which are obtained with the corresponding bases, in particular sodium hydroxide, potassium hydroxide or ammonium hydroxide.

Diastereoisomers can be separated into their racemic modifications in a known manner on the basis of the physicochemical differences of their constituents Racemates can be resolved by known methods, for example by recrystallising in optically active solvents, or by means of microorganisms or reaction with an optically active acid or base which forms a salt with the racemic compound, separation of the diastereoisomers by fractional crystallisation and liberation of the enantiomers by suitable agents. Particularly suitable optically active acids are, for example, the D- and L-forms of tartaric acid, ditoluoyltartaric acid, malic acid, mandelic acid, camphorsulphonic acid or pyrrolidone- carboxylic acid. Suitable optically active bases are α-phenylethylamine, menthylamine, ephedrine, brucine and quinine The more active of the antipodes is advantageously isolated. It is also possible, however, according to the invention to obtain the pure enantiomers by asymmetric synthesis.

The following examples serve to illustrate the invention.

EXAMPLE 1

2-Cyanamido-6,7-dihydro-7,7-dimethyl-3H,5H-pyrrolo-(2,3-f)benzimidazol-6-one 1 g (5.23 mmol) of 5,6-diamino-3,3-indolin-2-one is heated to reflux for six hours together with 1.24 g (5.23 mmol) of N-cyanodiphenoxy imidocarbonate in 20 ml of methanol. The reaction product is filtered off with suction, washed with isopropanol and dried.

Yield: 0.57 g (44% of theory), melting point above 300° C.

$C_{12}H_{11}N_5O$ (241.26)
Calc. C 59.74 H 4.60 N 29.03
Found C 59.21 H 4.73 N 28.94

EXAMPLE 2

2-Cyanamido-8,8-dimethyl-8-hydro-5H-imidazo(4,5-g)(3,1)-benzoxazin-6-one 1 g (4.8 mmol) of 6,7-diamino-4,4-dimethyl-4H-(3,1)-benzoxazin-2-one is reacted with 1.14 g (4.8 mmol) of N-cyanodiphenoxy imidocarbonate as described in Example 1 and the mixture is worked up.

Yield: 0.59 g (48% of theory), melting point above 300° C.

$C_{12}H_{11}N_5O_2$ (257.61)
Calc. C 55.94 H 4.30 N 27.33
Found C 55.51 H 4.20 N 27.15

EXAMPLE 3

2-Cyanamido-7,8-dihydro-3H,5H-imidazo(4,5-g)quinolin-6-one 1 g (5.6 mmol) of 6,7-diamino-3,4-dihydro-1H-quinolin-2-one is reacted together with 1.33 g (5.6 mmol) of n-cyanodiphenoxy imidocarbonate as described in Example 1 and the mixture is worked up.

Yield: 0.65 g (50% of theory), melting point above 300° C.

$C_{11}H_9N_5O$ (211.58)
Calc. C 62.44 H 4.29 N 33.27
Found C 62.49 H 4.20 N 33.19

EXAMPLE 4

2-((4-Difluoromethoxy)-3-pyridyl)-6,7-dihydro-7,7-dimethyl-3H,5H-pyrrolo(2,3-f)-benzimidazol-6-one 1.14 g (5.5 mmol) of 2-difluoromethoxynicotinoyl chloride dissolved in 5 ml o±dichloromethane are added dropwise to a suspension of 0.95 g (5 mmol) of 5,6-diamino-3,3-indolin-2-one in 5 ml of dichloromethane and 1.75 ml of triethylamine.

The mixture is stirred at room temperature for 8 hours. It is then concentrated to dryness in vacuo and the residue is treated with 100 ml of ethanol and 10 ml of concentrated hydrochloric acid and heated to reflux for 4 hours. The mixture is concentrated to dryness in vacuo, treated with ammonia until it gives an alkaline reaction and the residue is filtered off with suction.

Purification by column chromatography on silica gel follows. (Eluent: dichloromethane/methanol 90:10 v/v)

Yield: 0.60 g (35% of theory), melting point above 300° C.

$C_{17}H_{14}F_2N_4O_2$ (344.33)
Calc. C 59.30 H 4.10 F 11.04 N 16.27
Found C 58.30 H 4.25 F 10.61 N 15.89

EXAMPLE 5

2-(4-Pyridyl)-3H,5H-imidazo(4,5-g)quinolin-6-one 1 g (5.6 mmol) of 6,7-diamino-(4,5-g)-quinolin-2-one are dissolved in 10 ml of dichloromethane and treated with 2 g (20 mmol) of triethylamine. 1.06 g (6 mmol) of isonicotinoyl chloride, dissolved in 10 ml of dichloromethane, are added dropwise at 25° C. to this solution. The mixture is stirred at room temperature for 8 hours, concentrated and treated with water. The residue is taken up in 50 ml of ethanol, the solution is kept under reflux with 20 ml of concentrated hydrochloric acid for about 4 hours and concentrated, and the residue is rendered neutral with ammonia. It is filtered off with suction and recrystallised from ethanol.

Yield: 0.8 g (56% of theory), melting point above 300° C.

$C_{15}H_{12}N_4O$ (264.29)
Calc. C 68.17 H 4.58 N 21.20
Found C 68.00 H 4.62 N 21.14

EXAMPLE 6

Production of tablets and capsules

Tablets and capsules which contain the constituents given below are prepared by known procedures. These are suitable for the treatment of the abovementioned diseases, in particular cardiac insufficiency, in dosage amounts of one tablet or capsule each once to four times daily.

| Constituents | Weight (mg) Tablet | Capsule |
|---|---|---|
| 2-Cyanamido-6,7-dihydro-7,7-dimethyl-3H,5H-pyrrolo-(2,3-f)benzimidazol-6-one | 7 | 4 |
| Tragacanth | 10 | — |
| Lactose | 247.5 | 300 |
| Maize starch | 25 | — |
| Talc | 15 | — |
| Magnesium stearate | 2.5 | — |

EXAMPLE 7

Production of ampoules

Ampoules which contain the constituents mentioned in the following can be prepared in a known manner. Active substance and sodium chloride are dissolved in water and filled into glass ampoules under nitrogen.

| | |
|---|---|
| Sodium chloride | 18 mg |
| dist. water to | 2.0 ml |
| 2-Cyanamido-6,7-dihydro-7,7-dimethyl-3H,5H-pyrrolo-(2,3-f)benzimidazol-6-one fumarate | 1 mg |

EXAMPLE 8

A fat-based ointment is prepared using the constituents indicated (amounts by weight):
white petroleum jelly 76%
mobile paraffin 15%
glycerol 2%
emulsifier (polyoxyethylene-40-stearate) 2%
2-((4-Difluoromethoxy)-3-pyridyl)-6,8-dihydro-7,7-dimethyl-3H,5H-pyrrolo(2,3-f) -benzimidazol-6-one 5%.

Petroleum jelly, paraffin, glycerol and the emulsifier are heated to 80° C. The active substance is then added. The mixture is stirred until this has dissolved and the stirring is continued until the material becomes solid (ointment-like consistency).

The ointment is applied three times daily.

Test report

The novel compounds of the general formula I were investigated with respect to their cardiovascular properties.

For example, the compound 2-cyanamido-6,7-dihydro-7,7-dimethyl-3H,5H-pyrrolo(2,3-f)benzimidazol-6-one was investigated as follows:

The investigations were carried out using cats weighing 2.5-3.5 kg, which were anaesthetised with pentobarbital sodium (40 mg/kg i.p.). The animals were artificially ventilated.

To detect inotropic and chronotropic effects, the pressure in the left ventricle was measured using a tip catheter (Millar PC-350). From this, the contractility parameter dp/dtmax was recorded by means of an analogue differentiator and the heart rate (HR) by means of a rate counter.

The arterial blood pressure was measured in the femoral artery using a Statham pressure transducer (P 23 Db). The substance to be investigated was injected into the jugular vein. Dimethyl sulphoxide/polyethylene glycol was used as a solvent. The substance was investigated in 2-4 animals in each case at doses of 0.001, 0.01, 0.1 and 1 mg/kg i.v.

| Dose (mg/kg) | dp/dtmax (%) | HR (5) | mean arterial pressure |
|---|---|---|---|
| 0.001 | +10 | 0 | 0 |
| 0.01 | +37 | 0 | 0 |
| 0.1 | +56 | +3 | 0 |
| 1 | +67 | +8 | −15 |

Toxic side effects were not observed.

We claim:

1. A compound of the formula

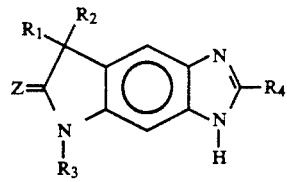

in which $R_1$ is hydrogen, $C_{1-6}$-alkyl, $C_{2-6}$-alkenyl or $C_{3-7}$-cycloalkyl, $R_2$ is hydrogen, $C_{1-6}$-alkyl, $C_{2-6}$-alkenyl or $C_{1-6}$-hydroxyalkyl, or $R_1$ and $R_2$ together with the carbon atom which carries them can be $C_{3-7}$-spiroalkyl, $R_3$ is hydrogen or $C_{1-6}$-alkyl, and $R_4$ is a cyanamido group, a 4-difluoromethoxy-3-pyridyl group or a $C_{1-2}$-nitroalkyl group, and Z is oxygen or sulphur, or a salt, tautomer or optical isomer thereof.

2. A compound according to claim 1, wherein such compound is 2-((4-difluoromethoxy)-3-pyridyl)-6,7-dihydro-7,7-dimethyl -3H,5H-pyrrolo(2,3-f)benzimidazol-6-one.

3. A compound according to claim 1, wherein such compound is 2-cyanamido-6,7-dihydro-7,7-dimethyl-3H,5H-pyrrolo(2,3-f)benzimidazol-6-one.

4. A composition for treatment and prophylaxis of cardiac insufficiency, an arterial thrombo embolism, an arterial occlusive disease, psoriasis, neurodermatitis, asthma, platelet aggregation or hypertension, which comprises a pharmaceutically effective amount of a compound or salt, tautomer or optical isomer thereof according to claim 1, and a pharmaceutically acceptable diluent.

5. A method of treatment of a patient with cardiac insufficiency, or hypertension, which comprises administering to such patient a pharmaceutically effective amount of a compound according to claim 1.

6. The method according to claim 5, wherein such compound is 2-((4-difluoromethoxy)-3-pyridyl)-6,7-dihydro-7,7-dimethyl-3H,5H-pyrrolo(2,3-f) benzimidazol-6-one, or 2-cyanamido-6,7-dihydro-7,7-dimethyl-3H,5H-pyrrolo(2,3-f)benzimidazol-6-one.

* * * * *

UNITED STATES PATENT AND TRADEMARK OFFICE
CERTIFICATE OF CORRECTION

PATENT NO. : 5,212,186
DATED : May 18, 1993
INVENTOR(S) : Pall, et al.

It is certified that error appears in the above-identified patent and that said Letters Patent is hereby corrected as shown below:

Title Page          ABSTRACT: Line 10 after " hydroxyalkyl, " insert -- or --

Signed and Sealed this

Eighteenth Day of October, 1994

Attest:

BRUCE LEHMAN

*Attesting Officer*      *Commissioner of Patents and Trademarks*